(12) United States Patent
Zaelke

(10) Patent No.: US 8,003,009 B2
(45) Date of Patent: Aug. 23, 2011

(54) FLUORESCENT AND VISIBLE PENETRANT INSPECTION

(75) Inventor: Arnold E. Zaelke, Rossmoor, CA (US)

(73) Assignee: Sherwin, Inc., South Gate, CA (US)

( * ) Notice: Subject to any disclaimer, the term of this patent is extended or adjusted under 35 U.S.C. 154(b) by 796 days.

(21) Appl. No.: 11/435,593

(22) Filed: May 17, 2006

(65) Prior Publication Data

US 2007/0267601 A1    Nov. 22, 2007

(51) Int. Cl.
*C09K 11/06* (2006.01)
(52) U.S. Cl. .................................. 252/301.19; 252/960
(58) Field of Classification Search ............. 252/301.19, 252/960
See application file for complete search history.

(56) References Cited

U.S. PATENT DOCUMENTS

| | | | |
|---|---|---|---|
| 3,429,826 A * | 2/1969 | Alburger | 252/301.19 |
| 3,716,492 A * | 2/1973 | Graham et al. | 252/301.19 |
| 3,935,731 A * | 2/1976 | Alburger | 73/104 |
| 4,049,568 A | 9/1977 | Molina | |
| 4,377,492 A | 3/1983 | Jones | |
| 4,392,982 A | 7/1983 | Molina | |
| 4,621,193 A | 11/1986 | Van Hoye | |
| 5,372,805 A * | 12/1994 | Finkel et al. | 424/59 |
| 6,311,538 B1 | 11/2001 | Martin | |
| 6,729,175 B2 | 5/2004 | Martin | |

FOREIGN PATENT DOCUMENTS

| | | |
|---|---|---|
| JP | 02-066437 | 6/1990 |
| JP | 29530212 | 9/1996 |

OTHER PUBLICATIONS

Pearson. The Safety of Fatty Acid Methyl Esters. www.apag.org/issues/methyl.html. Accessed on Dec. 2009. Published on Jan. 1997.*

* cited by examiner

*Primary Examiner* — C. Melissa Koslow
*Assistant Examiner* — Matthew E Hoban
(74) *Attorney, Agent, or Firm* — Kenneth L. Green

(57) ABSTRACT

An environmentally friendly penetrant used in non-destructive testing of material includes a vegetable oil fatty acid ester. A first embodiment of the penetrant is a post-emulsifiable fluorescent penetrant, a second embodiment of the penetrant is a heatable fluorescent penetrant, a third embodiment of the penetrant is a water washable fluorescent penetrant, a fourth embodiment of the penetrant is a visible water washable penetrant, and a fifth embodiment is a visible solvent removable penetrant. The heatable fluorescent penetrant includes a phenolic antioxidant to provide stability to at least approximately 120 degrees Fahrenheit. A method for using the heatable fluorescent penetrant includes heating the penetrant to lower penetrant viscosity and thus provide better penetration into flaws in the material.

21 Claims, 3 Drawing Sheets

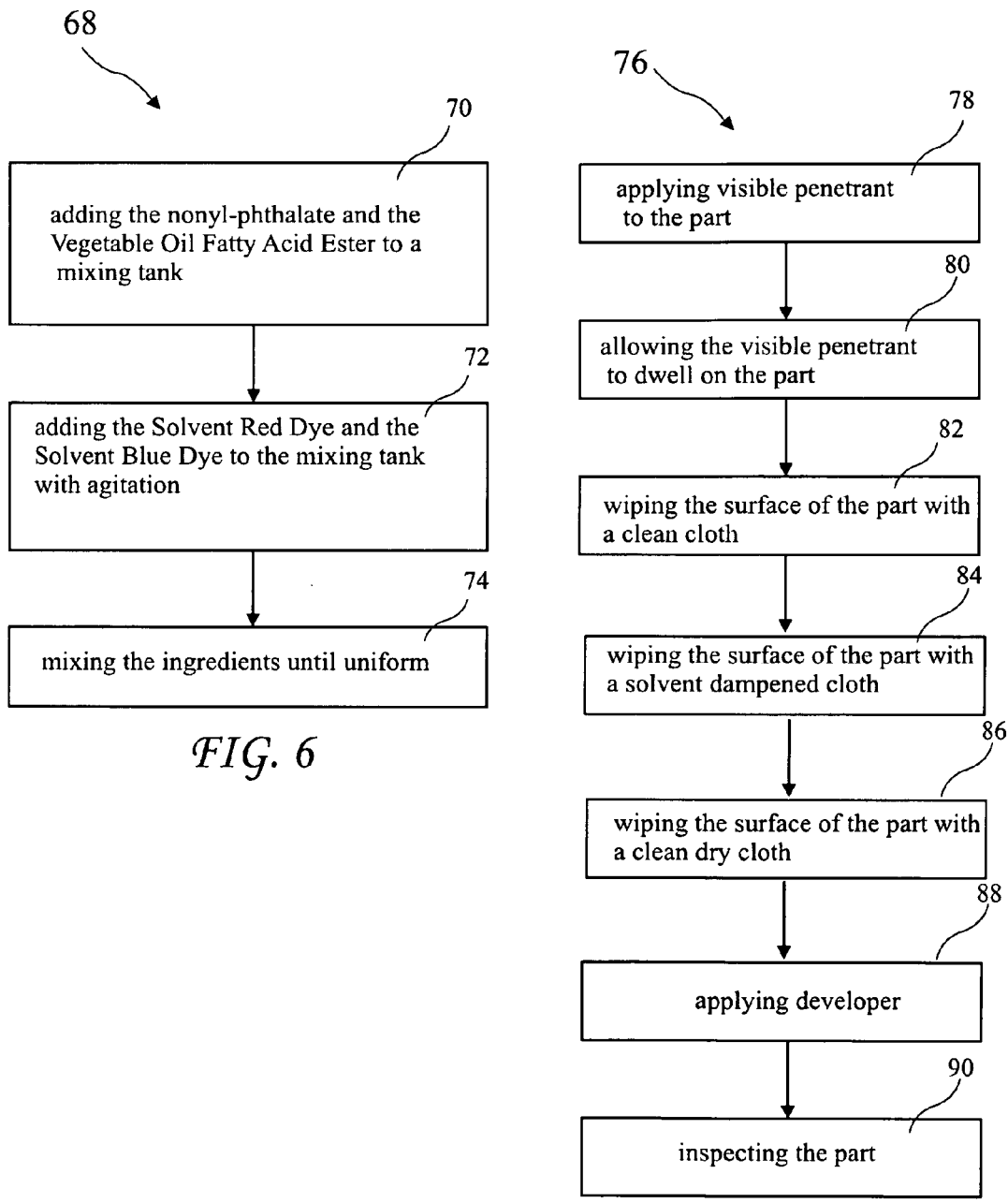

FLUORESCENT AND VISIBLE PENETRANT INSPECTION

BACKGROUND OF THE INVENTION

The present invention relates to the inspection of materials and in particular to the inspection of materials using a penetrant including a vegetable based fatty acid ester.

Fluorescent Penetrant Inspection (FPI) and Visible Penetrant Inspection VPI) are used to increase the visibility of a flaw in a material. FPI and VPI are performed by applying a penetrant solution to an inspection area on the surface of the material. The penetrant solution enters surface openings of the flaw. The inspection area is then wiped or rinsed to remove any penetrant solution residing on the surface of the material and a developer is applied to the inspection area. The developer draws the remaining penetrant material from the flaw opening. Flaws or cracks in the inspection area will then be visible under the influence of ultraviolet light (black light) when using a fluorescent penetrant or white light when using a visible penetrant. FPI and VPI are effective for detecting surface flaws in forgings, castings, extrusions, formed sections, webs, and skins of materials.

Known fluorescent penetrant solutions generally include petroleum distillates. Known visible penetrants used for VPI also include environmentally harmful petroleum distillates. Such petroleum distillates are environmentally harmful and require appropriate handling. Growing societal sensitivity to environmental issues has resulted in a need to find environmentally friendly alternatives.

Known fluorescent penetrant solutions also are sensitive to temperature. If such known fluorescent penetrant solutions are heated very much above ambient, the known fluorescent penetrant solutions breakdown. This sensitivity to temperature prevents heating the penetrant in applications of FPI which would benefit from heating the fluorescent penetrant.

BRIEF SUMMARY OF THE INVENTION

The present invention addresses the above and other needs by providing an environmentally friendly penetrant for use in non-destructive testing of materials, which penetrant includes a vegetable oil fatty acid ester in place of petroleum distillates. A first embodiment of the penetrant is a post-emulsifiable fluorescent penetrant, a second embodiment of the penetrant is a heatable fluorescent penetrant, a third embodiment of the penetrant is a water washable fluorescent penetrant, a fourth embodiment of the penetrant is a visible water washable penetrant, and a fifth embodiment is a visible solvent removable penetrant. The heatable fluorescent penetrant includes a phenolic antioxidant to provide stability to at least 120 degrees Fahrenheit. A method for using the heatable fluorescent penetrant includes heating the penetrant to lower penetrant viscosity and thus provide better penetration into flaws in the material.

In accordance with one aspect of the invention, there is provided a post-emulsifiable fluorescent penetrant preferably including between approximately 20 percent by weight and approximately 50 percent by weight of vegetable oil fatty acid ester, and more preferably including between approximately 20 percent by weight and approximately 30 percent by weight of vegetable oil fatty acid ester. The fluorescent penetrant further includes between approximately one percent by weight and approximately two percent by weight of a fluorescent dye, between approximately one percent by weight and approximately two percent by weight of bensoxazole derivative fluorescent brightener, between approximately 35 percent by weight and approximately 45 percent by weight of blend of phenyl phosphates, between approximately 20 percent by weight and approximately 30 percent by weight of phthalate ester, and between approximately three percent by weight and approximately five percent by weight of ethoxylated alcohol having a Hydrophile-Lipophile Balance (HLB) of between approximately 8.0 and approximately 8.5. The phenyl phosphates, may be a blend of moxo, di and triphenyl phosphates, and the phthalate ester may be di-nonyl phthalate ester. A heatable fluorescent penetrant preferably includes all the elements of the post-emulsifiable fluorescent penetrant, and further including preferably between approximately one percent by weight and approximately three percent by weight of phenolic antioxidant, and more preferably between approximately one percent by weight and approximately two percent by weight of phenolic antioxidant.

In accordance with another aspect of the invention, there is provided a method for inspecting a part using a heatable fluorescent penetrant. The method comprises heating the heatable penetrant, and maintaining temperature, immersing the part in the heated heatable penetrant for at least approximately five minutes, removing the part from the heated heatable penetrant, allowing the heated heatable penetrant to drain from the part, allowing the part to cool for at least approximately 10 minutes, pre-rinsing the part, emulsifying the surface penetrant, rinsing emulsified penetrant from the part, drying the part, applying developer to the part, allowing a developer dwell time of at least approximately 10 minutes, and inspecting the part.

In accordance with yet another aspect of the invention, there is a water washable fluorescent penetrant which contains approximately 0.25 percent by weight to approximately one percent by weight of a fluorescent dye, between approximately one percent by weight and approximately three percent by weight of a fluorescent brightener, between approximately forty and approximately sixty percent by weight of ethoxylated alcohol wetting agents, between approximately ten and approximately twenty percent by weight of a glycol ether and between approximately twenty and approximately thirty percent by weight of a vegetable oil fatty acid ester.

In accordance with another aspect of the invention there is a water washable visible penetrant which contains between approximately five percent by weight and approximately eight percent by weight of a combination of solvent red and blue dyes, between approximately twenty and approximately thirty percent by weight of an ethoxylated alcohol wetting agent having an HLB greater than approximately thirteen, approximately twenty percent by weight and approximately thirty percent by weight of a glycol ether, and between approximately 40 percent by weight and approximately 50 percent by weight of a vegetable oil fatty acid ester.

In accordance with another aspect of the invention there is a solvent removable visible penetrant which contains between approximately five percent by weight and approximately eight percent by weight of a combination of solvent red and blue dyes, between approximately twenty percent by weight and approximately forty percent by weight of a phthalate ester and between approximately fifty percent by weight and approximately seventy percent by weight of a vegetable oil fatty acid ester.

BRIEF DESCRIPTION OF THE SEVERAL VIEWS OF THE DRAWING

The above and other aspects, features and advantages of the present invention will be more apparent from the following more particular description thereof, presented in conjunction with the following drawings wherein:

FIG. 6 is a method for preparing a visible solvent removable penetrant.

FIG. 7 is a method for using the visible solvent removable penetrant.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing one or more preferred embodiments of the invention. The scope of the invention should be determined with reference to the claims.

Figure 1:
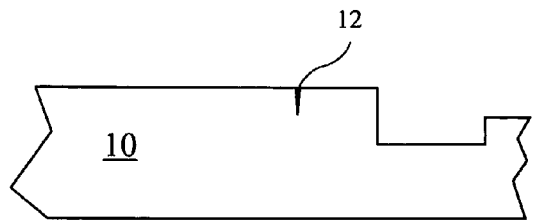
FIG. 1 is a method of use according to the present invention.

A penetrant according to the present invention includes as a new ingredient a vegetable oil fatty acid ester, which vegetable oil fatty acid ester is combined with other ingredients used in known penetrants. Additionally a heatable penetrant according to the present invention further includes an oxidation inhibitor not present in known penetrants. The penetrant is useful for the inspection of a part 10 to discover flaws or cracks 12 and the like as shown in FIG. 1. The vegetable oil fatty acid ester replaces environmentally unfriendly petroleum distillates (or solvents) used in known penetrants as a carrier for the dyes. The vegetable oil fatty acid ester has many of the physical properties of petroleum distillates, and thereby replaces petroleum distillates in the penetrant according to the present invention. The vegetable oil fatty acid ester has a low viscosity, thereby promoting better penetration of the material into surface flaws, and is not water soluble, thereby resisting removal from flaws 12 by a water rinse.

Additionally, the vegetable oil fatty acid ester has a greater affinity for developers than petroleum distillates, thereby generally increasing a penetrant's ability to locate flaws (i.e., provides increased sensitivity) and the vegetable oil fatty acid ester is essentially non-toxic, readily biodegradable, and easily obtained. An example of a suitable vegetable oil fatty acid ester is Soygold® industrial solvent available from AG Environmental Products in Lenexa, Kans.

Other elements of a penetrant according to the present invention include a dye and non-ionic wetting agents of the ethoxylated alcohol type. The penetrant may further include one or more of a phenolic antioxidant, phenyl phosphates, phthalate esters, and tripropylene glycol methyl ether.

The dye may be a fluorescent dye or a visible dye. When the penetrant is properly applied to a piece, and processed, the dyes, whether fluorescent or visible, remain in surface discontinuities following the cleaning of piece's surface. The fluorescent dyes are then detected when using ultraviolet light, with or without using a developer. The visible dyes may be viewed directly and may or may not require a developer, however, the use of a developer with visible dyes and fluorescent dyes is preferred.

The penetrant according to the present invention has at least five embodiments, a post-emulsifiable fluorescent penetrant, a heatable post-emulsifiable fluorescent penetrant, a water-washable fluorescent penetrant, a visible water washable penetrant, and a visible solvent removable penetrant. In each of the four embodiments, the vegetable oil fatty acid ester replaces petroleum distillates which are presently used. The constituents of each embodiment are shown in TABLE 1.

TABLE 1

| Four Embodiments of the Present Invention | | | | | |
|---|---|---|---|---|---|
| | post-emulsifiable fluorescent penetrants | heatable fluorescent penetrants | water-washable fluorescent penetrants | visible water washable penetrants | Visible solvent removable penetrants |
| Vegetable Oil Fatty Acid Ester | X | X | X | X | X |
| Phenolic Antioxidant | | X | | | |
| Dye | X | X | X | X | X |
| Phenyl Phosphates | X | X | | | |
| Di-nonyl Phthalate Esters | X | X | | | X |
| Ethoxylated Alcohol non-ionic wetting agent | X | X | X | X | |
| Tripropylene Glycol Methyl Ether | | | | | X |

The post-emulsifiable fluorescent penetrant according to the present invention preferably comprises (all percentages are approximate and by weight):

20% to 50% vegetable oil fatty acid ester;
1% to 2% naphthalimide fluorescent yellow dye;
1% to 2% bensoxazole derivative fluorescent brightener;
35% to 45% blend of moxo, di and triphenyl phosphates;
20% to 30% di-nonyl phthalate ester; and
3%-5% ethoxylated alcohol having a HLB of 8.0-8.5.

The heatable fluorescent penetrant preferably includes all the elements of the post-emulsifiable fluorescent penetrants, and further include preferably between approximately one percent by weight and approximately three percent by weight of phenolic antioxidant, and more preferably between approximately one percent by weight and approximately two percent by weight of phenolic antioxidant. The primary purpose of the phenolic antioxidant is to inhibit the heat-caused oxidation of the fluorescent dyes, thus prolonging the fluorescent properties of the dyes. As a result, the heatable fluorescent penetrant may be used at elevated temperatures, for example, to between approximately 130 degrees Fahrenheit and approximately 160 degrees Fahrenheit.

The phenyl phosphates serve as a solvent and carrier of fluorescent dyes. The phenyl phosphates are not water soluble, so they, and the dyes dissolved in them, will not easily be washed with water from flaws, when a water wash is used, with or without an emulsifier, to remove excess penetrant from a piece being inspected.

The di-nonyl phthalate esters serve a function similar to that of phenyl phosphates, however, di-nonyl phthalate esters are more a carrier for the dyes than a solvent for the dyes. Di-nonyl phthalate esters are not soluble in water, and resist removal from flaws.

Ethoxylated alcohol is a non-ionic wetting agent, facilitating the removal of penetrant from the surface of a piece being inspected, by using water, with or without an emulsifier, and more particularly to emulsify and remove the vegetable oil fatty acid ester from the surface of the piece being inspected. The particular ethoxylated alcohol used has limited water solubility, but aids the emulsification of water-insoluble components. Ethoxylated alcohol with a Hydrophilic/Lipophilic Balance (HLB) between approximately 8 and approximately 8.5 may be used with post emulsifiable fluorescent penetrants.

The visible water washable penetrant embodiment of the present invention preferably comprises (all percentages are approximate and by weight):
  5% to 7% Solvent Red Dye;
  0.1% to 1.0% Solvent Blue Dye;
  20% to 30% Non-ionic Wetting Agent Having HLB >13.0;
  20% to 30% Tripropylene Glycol Methyl Ether; and
  40% to 50% Vegetable Oil Fatty Acid Ester.

The visible solvent removable penetrant embodiment of the present invention preferably comprises (all percentages are approximate and by weight):
  5% to 7% solvent red dye;
  1% to 2% solvent blue dye;
  20% to 40% nonyl-phthalate ester; and
  50% to 70% vegetable fatty acid ester.

An ethoxylated alcohol with an HLB greater than approximately 13 is used with visible water washable penetrants. Tripropylene glycol methyl ether is a carrier and penetrating agent for the dyes used in the visible water washable penetrant. Different dye colors may be use, for example, red, orange, or purple.

Nonyl-phthalate and vegetable fatty acid esters are used as carriers and penetrating agents for the solvent dyes.

Figure 2:
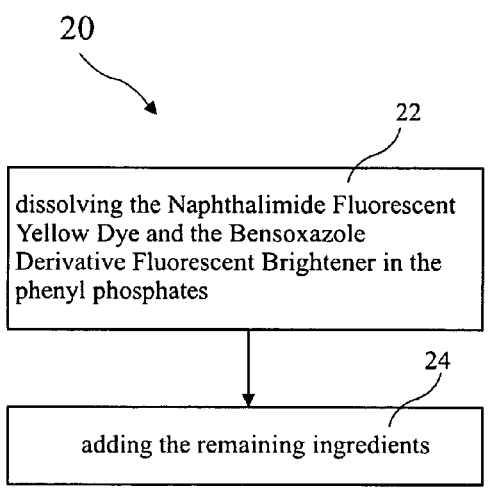
FIG. 2 is a method for preparing a post-emulsifiable penetrant.

A first method 20 for preparing the post-emulsifiable fluorescent penetrant is shown in FIG. 2. The method 20 comprises dissolving the Naphthalimide Fluorescent Yellow Dye and the Bensoxazole Derivative Fluorescent Brightener in the phenyl phosphates at a temperature of between approximately 120 degrees Fahrenheit and approximately 140 degrees Fahrenheit at step 22, and adding the remaining ingredients in the order presented above, with agitation at step 24. The heatable fluorescent penetrant may be prepared by adding the Phenolic Antioxidant at the step 22.

Figure 3:
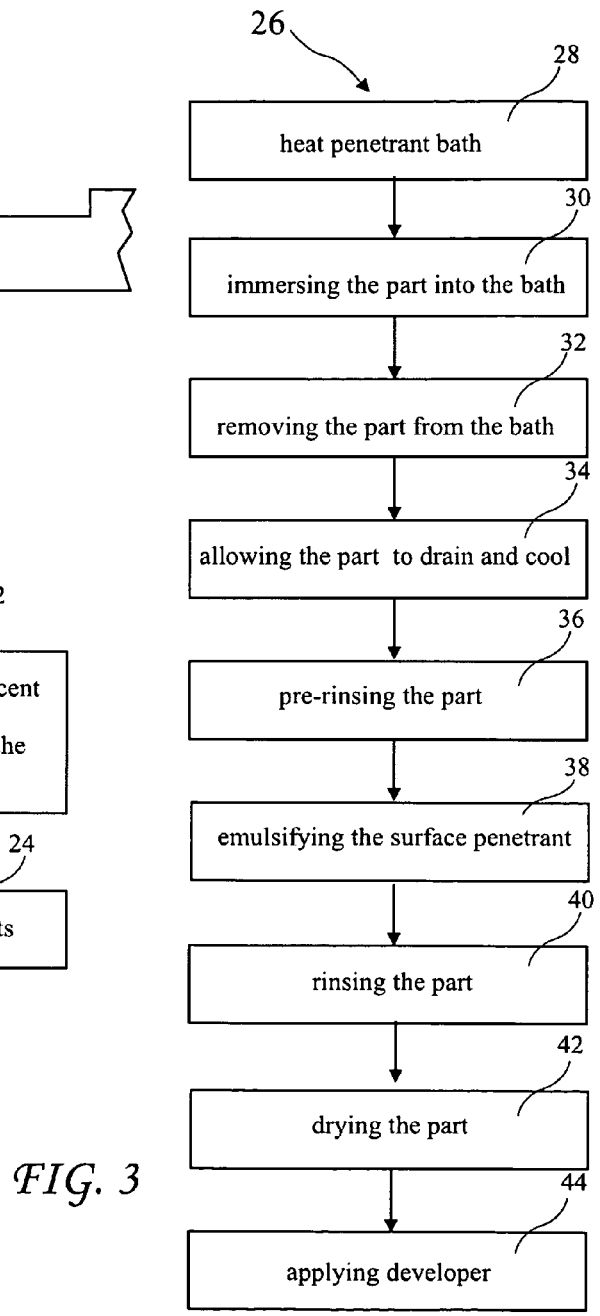
FIG. 3 is a method for using a heatable fluorescent penetrant.

A second method 26 for using the heatable fluorescent penetrant is described in FIG. 3. The method 26 comprises heating a penetrant bath to between approximately 130 degrees Fahrenheit and 160 degrees Fahrenheit with mechanical agitation to enhance mixing, and maintain temperature at step 28, immersing the part 10 (see FIG. 1) to be inspected in the heated bath for a minimum of approximately five minutes at step 30, removing the part 10 from the heated bath at step 32, allowing the part 10 to drain and cool for a minimum of approximately 10 minutes at step 34, pre-rinsing the part 10 at step 36, emulsifying the surface penetrant at step 38, rinsing the part 10 at step 40, drying the part at step 42, and applying developer per AMS-2644 at step 44. The method of use of the post-emulsifiable fluorescent penetrant is similar to the method of use for the heatable fluorescent penetrant, with the exception that the penetrant is not heated to between approximately 130 degrees Fahrenheit and 160 degrees Fahrenheit.

Figure 4:
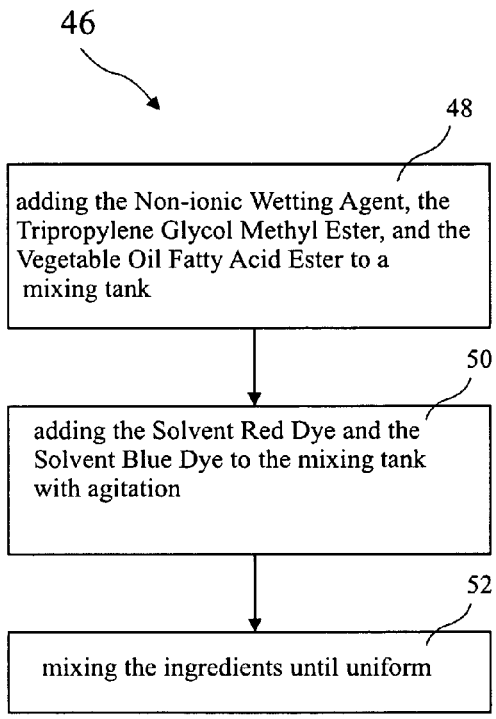
FIG. 4 is a method for preparing a visible water washable penetrant.

A third method 46 for preparing the visible penetrant is shown in FIG. 4. The method 46 comprises adding the Non-ionic Wetting Agent, the Tripropylene Glycol Methyl Ester, and the Vegetable Oil Fatty Acid Ester to a mixing tank at step 48, adding the Solvent Red Dye and the Solvent Blue Dye to the mixing tank with agitation at step 50, and mixing the ingredients until uniform at step 52.

Figure 5:
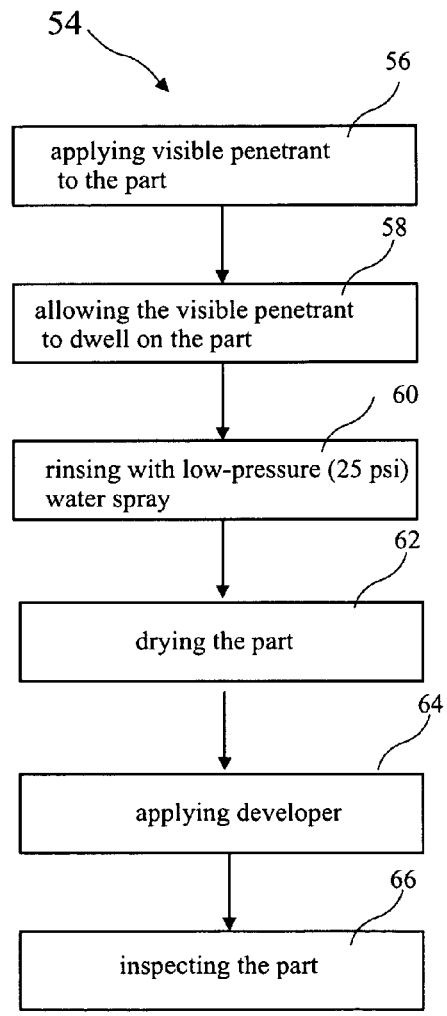
FIG. 5 is a method for using the visible water washable penetrant.

A fourth method 54 for using the visible penetrant is described in FIG. 5. The method 54 comprises applying visible penetrant to the part 10 to be inspected by immersion, spray, or brush at step 56, allowing the visible penetrant to dwell on the part 10 surface for approximately 10 minutes at step 58, rinsing with low-pressure (approximately 25 psi) water spray to remove penetrant from the surface, as prescribed in AMS-2644 at step 60, drying the part 10 at step 62, applying a developer at step 64, and inspecting the part 10 at step 66.

A method 68 for preparing the visible solvent removable penetrant is shown in FIG. 6. The method 68 comprises adding the nonyl-phthalate ester and vegetable fatty acid ester to a mixing tank at step 70, adding the solvent red and solvent blue dyes to the mixing tank at step 72 and mixing the ingredients until uniform at step 74.

A method 76 for using the visible solvent removable penetrant is described in FIG. 7. The method 76 comprises applying the visible penetrant to the part 10 to be inspected by immersion, spray or brush at step 78, allowing the visible penetrant to dwell on the part 10 for approximately 10 minutes at step 80, wiping the surface of part 10 with a clean cloth at step 82, wiping the surface of part 10 with a clean cloth dampened with solvent at step 84, wiping the surface of part 10 with a dry clean cloth to remove solvent residue at step 86, apply developer at step 88 and inspect the part 10 at step 90.

While the invention herein disclosed has been described by means of specific embodiments and applications thereof, numerous modifications and variations could be made thereto by those skilled in the art without departing from the scope of the invention set forth in the claims.

I claim:

1. A penetrant comprising:
  a solvent comprising between approximately 20 percent by weight and approximately 50 percent by weight of vegetable oil fatty acid ester;
  dye; and
  between approximately 35 percent by weight and approximately 45 percent by weight of blend of phenyl phosphates.

2. The penetrant of claim 1, wherein the solvent consists essentially of between approximately 20 percent by weight and approximately 30 percent by weight of vegetable oil fatty acid ester.

3. The penetrant of claim 1, wherein the penetrant is a heatable post-emulsifiable fluorescent penetrant further including a phenolic antioxidant thereby allowing the penetrant to be heated above ambient temperature for better penetration while remaining stable.

4. The penetrant of claim 1, wherein the penetrant is a post-emulsifiable fluorescent penetrant wherein:
the dye is a fluorescent dye; and
including at least three percent by weight of a wetting agent.

5. The penetrant of claim 3, wherein the phenolic antioxidant comprises between approximately one percent by weight and approximately three percent by weight of the phenolic antioxidant thereby allowing the penetrant to be heated to at least approximately 130 degrees Fahrenheit.

6. A visible water washable penetrant consisting essentially of:
between approximately 40 percent by weight and approximately 50 percent by weight of a Vegetable Oil Fatty Acid Ester;
between approximately 5 percent by weight and approximately 8 percent by weight of a Dye;
between approximately 20 percent by weight and approximately 30 percent by weight of a Wetting agent; and
between approximately 20 percent by weight and approximately 30 percent by weight of a Carrier and Penetrant Agent comprising Tripropylene Glycol Methyl Ether.

7. The visible water washable penetrant of claim 6, wherein the Wetting agent is a Non-ionic Wetting agent having Hydrophilic/Lipophilic Balance (HLB) greater than 13.0.

8. The penetrant of claim 7, wherein the Non-ionic Wetting agent is ethoxylated alcohol.

9. A post-emulsifiable fluorescent penetrant comprising:
between approximately 20 percent by weight and approximately 50 percent by weight of vegetable oil fatty acid ester
between approximately one percent by weight and approximately two percent by weight of fluorescent dye;
between approximately one percent by weight and approximately two percent by weight of fluorescent brightener;
between approximately 35 percent by weight and approximately 45 percent by weight of blend of phenyl phosphates;
between approximately 20 percent by weight and approximately 30 percent by weight of phthalate ester; and
between approximately three percent by weight and approximately five percent by weight of ethoxylated alcohol wetting agent.

10. The post-emulsifiable fluorescent penetrant of claim 9, wherein the fluorescent dye comprises naphthalimide fluorescent yellow dye.

11. The penetrant of claim 1, further including at least three percent by weight of a wetting agent.

12. The penetrant of claim 11, wherein the wetting agent is ethoxylated alcohol.

13. The penetrant of claim 1, including between approximately 20 percent by weight and approximately 30 percent by weight of phthalate ester.

14. A post-emulsifiable fluorescent penetrant comprising:
between approximately 20 percent by weight and approximately 50 percent by weight vegetable oil fatty acid ester;
between approximately one percent by weight and approximately 2 percent by weight naphthalimide fluorescent yellow dye;
between approximately one percent by weight and approximately 2 percent by weight bensoxazole derivative fluorescent brightener;
between approximately 35 percent by weight and approximately 45 percent by weight blend of moxo, di and triphenyl phosphates;
between approximately 20 percent by weight and approximately 30 percent by weight di-nonyl phthalate ester; and
between approximately 3 percent by weight and approximately 5 percent by weight ethoxylated alcohol having a Hydrophilic/Lipophilic Balance (HLB) of between approximately 8.0 and approximately 8.5.

15. The penetrant of claim 14, wherein the penetrant is a heatable post-emulsifiable fluorescent penetrant further including between approximately one percent by weight and approximately three percent by weight of phenolic antioxidant, whereby the heatable fluorescent penetrant may be used at elevated temperatures exceeding approximately 130 degrees Fahrenheit to obtain better penetration of materials being inspected.

16. The penetrant of claim 14, wherein:
the penetrant is at an elevated temperature between approximately 130 degrees Fahrenheit and approximately 160 degrees Fahrenheit to obtain better penetration of materials being inspected; and
the penetrant further includes between approximately one percent by weight and approximately three percent by weight of phenolic antioxidant to obtain stability at elevated temperatures.

17. A heatable fluorescent penetrant comprising:
between approximately 20 percent by weight and approximately 50 percent by weight of vegetable oil fatty acid ester;
between approximately one percent by weight and approximately two percent by weight of fluorescent dye;
between approximately one percent by weight and approximately two percent by weight of fluorescent brightener;
between approximately 35 percent by weight and approximately 45 percent by weight of blend of phenyl phosphates;
between approximately 20 percent by weight and approximately 30 percent by weight of di-nonyl phthalate ester;
between approximately three percent by weight and approximately five percent by weight of ethoxylated alcohol wetting agent having a Hydrophilic/Lipophilic Balance (HLB) of between 8.0 and 8.5; and
a phenolic antioxidant thereby allowing the penetrant to be heated above ambient temperature for better penetration while remaining stable.

18. The penetrant of claim 17, wherein the phenolic antioxidant provides stability to the penetrant to at least 120 degrees Fahrenheit.

19. The penetrant of claim 17, wherein the phenolic antioxidant comprises between approximately one percent by weight and approximately three percent by weight of the phenolic antioxidant thereby allowing the penetrant to be heated to at least approximately 130 degrees Fahrenheit.

20. A visible water washable penetrant comprising:
between approximately 20 percent by weight and approximately 50 percent by weight of vegetable oil fatty acid ester;

between approximately five percent by weight and approximately eight percent by weight of visible dye;

between approximately twenty percent by weight and approximately thirty percent by weight of ethoxylated alcohol wetting agent;

between approximately twenty percent by weight and approximately thirty percent by weight of Tripropylene Glycol Methyl Ether.

21. The penetrant of claim 20, wherein the visible dye comprises:

approximately five percent by weight to approximately seven percent by weight solvent red dye; and approximately 0.1 percent by weight to approximately one percent by weight solvent blue dye.

* * * * *